US012589077B2

(12) United States Patent
Guillaneuf et al.

(10) Patent No.: US 12,589,077 B2
(45) Date of Patent: *Mar. 31, 2026

(54) METHOD FOR PREPARING BIODEGRADABLE MICROCAPSULES AND MICROCAPSULES THUS OBTAINED

(71) Applicant: GEM INNOV, Gemenos (FR)

(72) Inventors: Yohann Guillaneuf, Marseilles (FR); Catherine Lefay, Marseilles (FR); Didier Gigmes, Allauch (FR); The Hien Ho, Marseilles (FR); Kaouthar Oudoua, Marseilles (FR); Thierry Ribeiro, La Fare les Oliviers (FR); Yves Ortais, Gemenos (FR)

(73) Assignee: GEM INNOV, Gemenos (FR)

( * ) Notice: Subject to any disclaimer, the term of this patent is extended or adjusted under 35 U.S.C. 154(b) by 407 days.

This patent is subject to a terminal disclaimer.

(21) Appl. No.: 18/251,744

(22) PCT Filed: Nov. 18, 2021

(86) PCT No.: PCT/IB2021/060689

§ 371 (c)(1),
(2) Date: May 4, 2023

(87) PCT Pub. No.: WO2022/107032

PCT Pub. Date: May 27, 2022

(65) Prior Publication Data

US 2024/0016751 A1 Jan. 18, 2024

(30) Foreign Application Priority Data

Nov. 18, 2020 (FR) ....................................... 2011829

(51) Int. Cl.

| | |
|---|---|
| ***A61K 9/50*** | (2006.01) |
| ***A01N 25/28*** | (2006.01) |
| ***A01P 1/00*** | (2006.01) |
| ***A01P 3/00*** | (2006.01) |
| ***A61K 8/11*** | (2006.01) |
| ***C09D 5/00*** | (2006.01) |
| ***C09J 9/00*** | (2006.01) |

(52) U.S. Cl.

CPC ............ *A61K 9/5031* (2013.01); *A01N 25/28* (2013.01); *A01P 1/00* (2021.08); *A01P 3/00* (2021.08); *A61K 8/11* (2013.01); *A61K 9/5026* (2013.01); *A61K 9/5089* (2013.01); *C09D 5/00* (2013.01); *C09J 9/00* (2013.01)

(58) Field of Classification Search

None

See application file for complete search history.

(56) References Cited

U.S. PATENT DOCUMENTS 6,569,528 B2 5/2003 Nam et al.
6,998,115 B2 2/2006 Langer et al.
7,119,057 B2 10/2006 Popplewell et al.
7,294,612 B2 11/2007 Popplewell et al.
7,427,394 B2 9/2008 Anderson et al.
7,585,824 B2 9/2009 Popplewell et al.
7,736,695 B2 6/2010 Schwantes et al.
7,799,752 B2 9/2010 Ness et al.
7,803,422 B2 9/2010 Schwantes et al.
7,985,445 B2 7/2011 Schwantes et al.
8,071,082 B2 12/2011 Zugates et al.
8,168,225 B2 5/2012 Casana Giner et al.
RE43,612 E 8/2012 Anderson et al.
8,287,849 B2 10/2012 Langer et al.
8,455,098 B2 6/2013 Schwantes
8,557,231 B2 10/2013 Langer
8,562,966 B2 10/2013 Zugates et al.
8,685,446 B2 4/2014 Casana Giner et al.
8,715,544 B2 5/2014 Schwantes
8,877,217 B2 11/2014 Kim et al.
8,911,783 B2 12/2014 Casana Giner et al.
9,079,152 B2 7/2015 Markus et al.
9,101,143 B2 8/2015 Markus et al.
9,101,666 B2 8/2015 Langer et al.
9,192,908 B2 11/2015 Schwantes
9,272,043 B2 3/2016 Saltzman et al.
9,567,430 B2 2/2017 Saltzman et al.
(Continued)

FOREIGN PATENT DOCUMENTS

CN 103230766 B 12/2014
CN 105646911 A 6/2016
(Continued)

OTHER PUBLICATIONS

International Search Report dated Jan. 28, 2022, corresponding to PCT/IB2021/060689.

Jae-Seung Lee et al. "Gold, Poly(beta-amino ester) Nanoparticles for Small Interfering RNA Delivery" Nano Leiters, American Chemical Society, US, vol. 9, No. 6, Jun. 10, 2009, pp. 2402-2406, XP002629297.

Dinesh Shenoy et al. "Poly(ethylene oxide)-Modified Poly(beta-amino ester) Nanoparticles as a pH-Sensitive System for Tumor-Targeted Delivery of Hydrophobic Drugs. 1. In Vitro Evaluations", Molecular Pharmaceutics, vol. 2, No. 5, Oct. 31, 2005, pp. 357-366, XP055212460.

Maurya et al. A Review on Acrylate Terminated Urethane Oligomers and Polymers: Synthesis and Applications, Polymer-Plastics Technology and Engineering, 57, 7, 625-656 (2018).

(Continued)

*Primary Examiner* — Anna R Falkowitz
*Assistant Examiner* — Garen Gotfredson
(74) *Attorney, Agent, or Firm* — Ladas & Parry LLP; Malcolm J. MacDonald

(57) ABSTRACT

Method for manufacturing microcapsules comprising a wall made of polymer material containing an active substance, comprising the following steps: —preparing an oil phase comprising a poly(beta-aminoester) prepolymer, and an active substance constituting the phase to be encapsulated; preparing an aqueous phase comprising at least one surfactant; preparing an O/W (oil in water) emulsion by adding the oil phase to the aqueous phase; and initiating radical polymerisation with in the emulsion. A polymerisation initiator must be present in the aqueous and/or oil phase.

14 Claims, 1 Drawing Sheet

(56) References Cited

U.S. PATENT DOCUMENTS

| | | | |
|---|---|---|---|
| 9,687,569 | B2 | 6/2017 | Zhang et al. |
| 9,700,627 | B2 | 7/2017 | Langer et al. |
| 9,895,451 | B2 | 2/2018 | Saltzman et al. |
| 9,944,886 | B2 | 4/2018 | Hitchcock |
| 9,944,887 | B2 | 4/2018 | Tasker et al. |
| 9,951,293 | B2 | 4/2018 | Hitchcock et al. |
| 9,951,294 | B2 | 4/2018 | Hitchcock et al. |
| 9,962,321 | B2 | 5/2018 | Baxter et al. |
| 10,335,500 | B2 | 7/2019 | Hanes et al. |
| 10,465,042 | B2 | 11/2019 | Cui et al. |
| 10,682,422 | B2 | 6/2020 | Saltzman et al. |
| 2005/0043209 | A1 | 2/2005 | Schmiedel et al. |
| 2005/0244504 | A1 | 11/2005 | Little |
| 2010/0086603 | A1 | 4/2010 | Shirley et al. |
| 2011/0020648 | A1 | 1/2011 | Fukazawa et al. |
| 2011/0057340 | A1 | 3/2011 | Perichaud |
| 2011/0268778 | A1 | 11/2011 | Dihora et al. |
| 2011/0269657 | A1 | 11/2011 | Dihora et al. |
| 2014/0037703 | A1 | 2/2014 | Dihora et al. |
| 2016/0184196 | A1 | 6/2016 | Baxter |
| 2017/0283830 | A1 | 10/2017 | Saltzman |
| 2018/0000968 | A1 | 1/2018 | Oh et al. |
| 2018/0078468 | A1 | 3/2018 | Jerri |
| 2018/0360706 | A1 | 12/2018 | Dihora et al. |
| 2019/0134592 | A1 | 5/2019 | Rost et al. |
| 2019/0194444 | A1 | 6/2019 | Capasso Palmiero et al. |
| 2019/0224638 | A1 | 7/2019 | Schwantes |
| 2019/0275490 | A1 | 9/2019 | Bachawala |
| 2020/0113821 | A1 | 4/2020 | Saltzman |
| 2020/0122110 | A1 | 4/2020 | Zhang et al. |
| 2020/0123219 | A1 | 4/2020 | Hutchinson |
| 2020/0129947 | A1 | 4/2020 | Ouali et al. |
| 2020/0164332 | A1 | 5/2020 | Demoulin |
| 2020/0172663 | A1 | 6/2020 | Katzmarek |
| 2020/0360889 | A1 | 11/2020 | Ortais et al. |

FOREIGN PATENT DOCUMENTS

| | | | |
|---|---|---|---|
| CN | 110559448 | A | 12/2019 |
| EP | 1084860 | A2 | 3/2001 |
| EP | 1928594 | B1 | 1/2015 |
| EP | 2913103 | A1 | 9/2015 |
| EP | 1991052 | B1 | 9/2017 |
| EP | 2994318 | B1 | 7/2019 |
| JP | 4200764 | B2 | 12/2008 |
| WO | 03/016369 | A1 | 2/2003 |
| WO | 2007/070118 | A1 | 6/2007 |
| WO | 2009/115671 | A1 | 9/2009 |
| WO | 2013/144025 | A1 | 8/2013 |
| WO | 2019121736 | A1 | 6/2019 |
| WO | 2019121738 | A1 | 6/2019 |
| WO | 2020009439 | A1 | 1/2020 |

OTHER PUBLICATIONS

Hodnett et al. Journal of Polymer Science: A Study of the Mechanism of Interfacial Polyamidation and Polyesterification, vol. 58, pp. 1415-1421 (1962).

Brey et al. Elsevier—Controlling poly(b-amino ester) network properties throughmacromer branching, Acta Biomaterialia 4 (2008) 207-217.

Brey et al.—Influence of macromer molecular weight and chemistry on poly(b-amino ester) network properties and initial cell interactions—Department of Bioengineering, University of Pennsylvania (2007).

Lynn et al.—J. Am. Chem. Soc.—Degradable Poly(â-amino esters): Synthesis, Characterization, and Self-Assembly with Plasmid DNA (2000).

Roux et al.—ACS Macro Letters—Facile and Rapid Access to Glyconanocapsules by CuAAC Interfacial Polyaddition in Miniemulsion Conditions (2012).

Liao et al.—Journal of Applied Polymer Science—Fragrance-containing microcapsules based on interfacial thiol-ene polymerization (2016).

Amato et al.—ACS Applied Materials and Interfaces—Functional Microcapsules via Thiol-Ene Photopolymerization in Droplet-Based Microfluidics (2020).

Morgan et al.—Journal of Polymer Science—Interfacial Polycondensation. 11. Fundamentals of Polymer Formation at Liquid Interfaces—vol. XL, pp. 299-327 (1959).

Eareckson, III—Journal of Polymer Science—Interfacial Polycondensation—vol. XL, pp. 399-406 (1959).

Cheng et al.—Bio Macromolecules—Michael Addition Polymerization of Trifunctional Amine and Acrylic Monomer: A Versatile Platform for Development of Biomaterials (2016).

Li et al. Elsevier—Int. Journal of Pharmaceutics—Microencapsulation by solvent evaporation: State of the art for process engineering approaches (2008).

Liu et al.—Advanced Healthcare Materials—Poly(β-Amino Esters): Synthesis, Formulations, and Their Biomedical Applications (2019).

Little et al.—MIT—Poly-β amino ester-containing microparticles enhance the activity of nonviral genetic vaccines (2004).

Wu et al.—Polymers for Advanced Technologies—Preparation of biodegradable microcapsules through an organic solvent-free interfacial polymerization method (2018).

Safranski et al.—Elsevier—The effect of chemistry on the polymerization, thermo-mechanical properties and degradation rate of poly(β-amino ester) networks (2010).

Siebert et al.—Chem. Comm.—Towards copper-free nanocapsules obtained by orthogonal interfacial "click" polymerization in miniemulsion (2012).

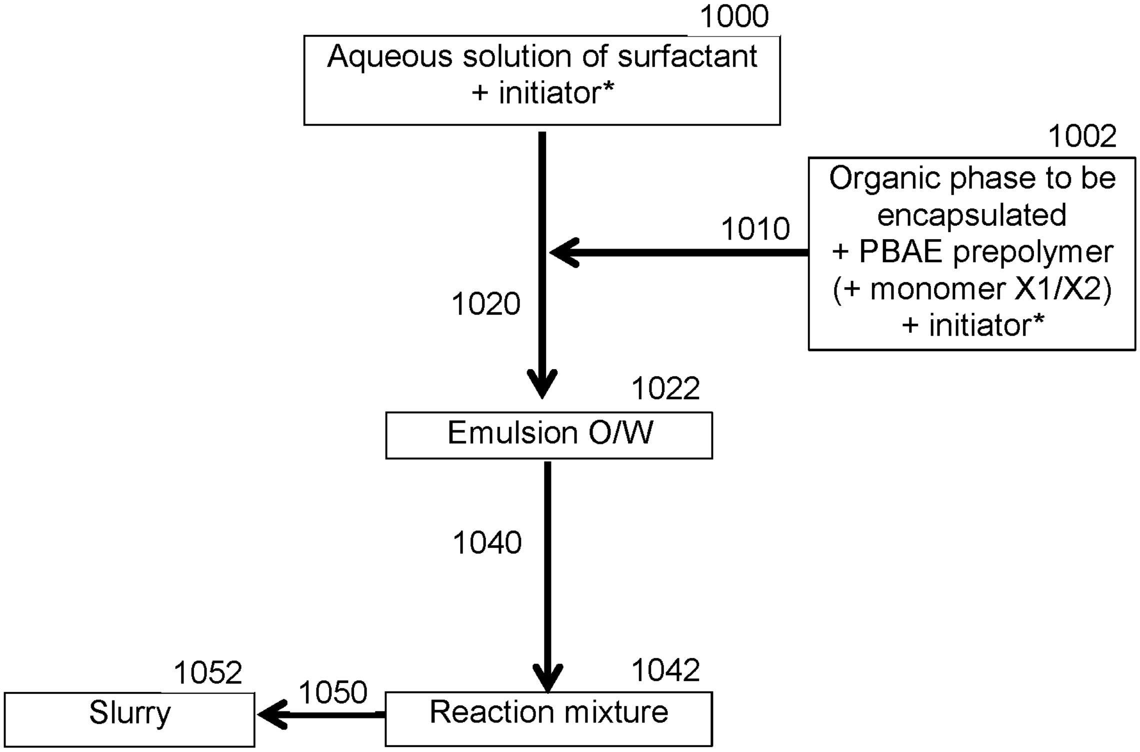
1000
Aqueous solution of surfactant + initiator*
1002
Organic phase to be encapsulated + PBAE prepolymer (+ monomer X1/X2) + initiator*
1010
1020
1022
Emulsion O/W
1040
1042
Reaction mixture
1050
1052
Slurry

METHOD FOR PREPARING BIODEGRADABLE MICROCAPSULES AND MICROCAPSULES THUS OBTAINED

TECHNICAL FIELD OF THE INVENTION

The present description relates to the field of microcapsules, and more particularly to methods for manufacturing microcapsules with a view to enclosing active substances actives such as essential oils. More specifically, it relates to a method for preparing biodegradable microcapsules. This method performs radical polymerization of multifunctional compounds in an emulsion of the type O/W (Oil in Water) resulting in a wall of the cross-linked poly(beta-amino ester) type which is biodegradable. The invention also relates to biodegradable microcapsules obtained with this method.

PRIOR ART

Microencapsulation is a method for protecting a reactive, sensitive or volatile substance (referred to here as "active ingredient") in a capsule in which the size can vary from a nanometer to a micrometer. The core of the capsule is therefore isolated from the external environment thereof by a wall. This makes it possible to delay the evaporation, release or degradation thereof; there are numerous applications which make use of these technical effects when the microcapsules are incorporated in a complex formulation or applied to a product.

For example, microcapsules can be used to disperse in a controlled manner the active ingredient contained therein, which can particularly be a biocidal agent, an insecticide, a disinfectant, or a fragrance; this can take place by diffusion through the wall or under the influence of an external force which ruptures the wall. In some applications, the release of the active ingredient takes place under the influence of an external force which breaks the wall of the microcapsules; thus, it is possible to release an adhesive (see for example WO 03/016369—Henkel), or a reagent (see for example WO 2009/115671—Catalyse).

In further applications, the contents of the microcapsule cannot escape but the color change thereof under the effect of a variation of temperature (thermochromism) or of UV radiation (photochromism) is outwardly visible (see for example WO 2013/114 025—Gem Innov, or WO 2007/070118—Kimberly-Clark, or EP 1 084 860—The Pilot Ink Co.).

There are several techniques for preparing microcapsules. The main ones are spray-drying, interfacial polymerization, solvent evaporation, polymer self-assembly using the Layer-by-Layer (LbL) technique, and colloidosome preparation. All these techniques make it possible to obtain stable microcapsules of a mean diameter of about 10 μm. Interfacial polymerization is nevertheless the predominant technique as it enables quick preparation in a single step of microcapsules in which the wall is strong enough for the latter to be isolated and thus be used in numerous applications.

Several polymer families are conventionally used for manufacturing the wall of microcapsules (Perignon, C. et al., Journal of Microencapsulation 2015, 32 (1), 1-15), such as polyamides (PA), polyurethanes (PU) or polyureas. The preparation of PA microcapsule walls generally uses monomers of the diamine (hexamethylene diamine for example) and acyl chloride (sebacoyl chloride for example) type, whereas those in PU make use of monomers of the di-isocyanate (HDI, IPDI etc.) and diol type. In the case of polyureas, di-isocyanate and diamine type monomers or di-isocyanates alone are used wherein the hydrolysis at the interface produces amines enabling urea function synthesis.

For example, the document WO 2009/115671 cited above describes the formation of microcapsule walls by interfacial polycondensation, using different monomer mixtures: hexamethylene diisocyanate (HMDI) and ethylene diamine; tetraethylorthosilicate (TEO) and 3-(trimethoxysilyl)propylmethacrylate (MPTS); 2,4-tolylenediisocyanate (TDI) and 1,3 phenylenediamine; 2,4-toluene diisocyanate and 1,3-phenylene diamine.

There are already some works reporting the preparation of microcapsules by interfacial polymerization using other types of polymers. Mention can be made for example of the works by J. Bernard on the preparation of glyconanocapsules by copper-catalyzed azide-alkyne cycloaddition (R. Roux et al., J. ACS Macro Lett. 2012, 1 (8), 1074-1078), or the works by K. Landfester (Siebert et al. Chem. Commun. 2012, 48, 5470-5472). L. Shi et al. (J. Appl. Polym. Sci. 2016, 133 (36), 168-7) and D. Patton et al. (ACS Appl. Mater. Interfaces 2017, 9 (4), 3288-3293) who also prepared microcapsules by thiol-ene chemistry initiated by respectively a base and a photoinitiator.

The disadvantage of interfacial polymerization is the possibility of side reactions between the amine and a carbonyl group. Thus, depending on the monomers employed and the reaction conditions chosen, interfacial polymerization can lead to mixtures of polymers which are quite complex.

It is known that radical polymerization can lead to polymers of good purity, or with fewer side reactions, than other polymerization techniques. Patent application US 2015/0017214 A1 (Tagasago) describes a process for manufacturing microcapsules by radical polymerization in which two or three types of vinyl monomers are introduced into the hydrophobic (core) phase of an O/W type emulsion (Oil in Water). A radical initiator is also added to carry out the polymerization in the bulk of the emulsion. This process uses at least three types of monomers: a hydrophilic monomer (for example methacrylic acid) to bring the growing polymer towards the interface, a hydrophobic monomer to vary the mechanical properties of the wall of the microcapsules, and a compound of the type di or tri (meth) acrylate to obtain a crosslinked material.

In general, a relatively broad spectrum of polymeric materials is therefore proposed to a person skilled in the art to select the suitable type of microcapsule for a given use. Thus, microcapsules are already used in numerous technical applications, but the application potential thereof has not yet been fully recognized, and it is a strongly emerging sector destined to grow significantly once the microcapsule wall meets increasingly stringent criteria in terms of toxicity and recyclability.

However, microcapsules represent microparticles of polymeric materials. For some years, polymeric material microparticles have been identified as an area of environmental concern, due to the wide dissemination thereof in ecosystems, in soils, in aquatic and maritime ecosystems, reaching distant locations from the place where they were introduced into the ecosystem. This wide dissemination harms not only as a general rule the organisms present in these ecosystems, but could also have harmful effects for human health. Increasingly stringent regulations are already being announced which restrict the use of plastics capable of forming microparticles during the degradation thereof in-situ in a natural environment, and especially of plastics used directly in the form of microparticles.

For environmental reasons, it may seem contradictory to seek to develop a novel product consisting of polymeric microparticles. It has hence emerged as desirable to have microcapsules made of degradable polymeric material. It is noted that microcapsules, used in numerous special applications and capable of being incorporated in numerous products in common use (such as textile materials, cosmetic or phytosanitary products) or technical use (such as paints, varnishes, inks), will not normally undergo end-of-life collection, and therefore cannot undergo biodegradation by composting, as can be envisaged for collected plastic products. Thus, the degradability of the plastics forming the wall of microcapsules cannot be based on chemical mechanisms which take place during composting. In this context, the question as to whether the degradability of the microcapsules involves a biological mechanism is somewhat unimportant; what is important is the degradability thereof in an ecosystem, regardless of the chemical mechanism of this degradation. For example, a fermentation would be a biodegradation, while a simple degradation in an ecosystem under the effect of light could be a photochemical reaction independent of the ecosystem; in reality, the situation will often be a combination, especially if the degradation takes place in stages. We use the expression "(bio)degradable" hereinafter to denote the characteristic of a material of degrading in a natural environment on a relatively brief scale (of the order of weeks or a year), according to the characteristics of this natural environment and the exposure of the material to the various agents present in this natural environment.

It is observed that all the microcapsules previously developed result in the preparation of polymer chains (polyamide, polyurea, polyurethane, etc.) which will be either physically interlocked in the case of a reaction between bifunctional compounds, or crosslinked in the case of one or more multifunctional compounds (functionality 3). In any case, the walls are not (bio)degradable due to the nature of the polymer chain.

The problem addressed by the present invention is that of providing a novel type of microcapsules, which is easy to synthesize, without making use of toxic and/or costly raw materials, is (bio)degradable in the natural environment, can be used with a large number of active ingredients, leads to polymers which are rather pure, and provides good external protection for the active ingredient that it is intended to contain.

SUBJECT MATTER OF THE INVENTION

During their research work, the inventors discovered that one possibility for obtaining degradable microcapsules would be to prepare walls made of polyester, which is a polymer known for the (bio)degradability thereof. The literature shows that studies have already been conducted on this theme, and it has been demonstrated that the rate of reaction between acid chlorides and diols was very slow. This system is thus unsuitable for interfacial polymerization (see E. M. Hodnett and D. A. Holmer, J Polym Sci, 1962, 58, 1415-21). Specific conditions such as the use of bisphenol A as diol and/or a reaction at very high pH made it possible to obtain microcapsules (see W. Eareckson, J Polym Sci, 1959, 399-406; see also P. W. Morgan and S. L. Kwolek, J Polym Sci, 1959, 299-327) but these conditions are overly restrictive for numerous internal phases and/or applications. Furthermore, the slow rate of polymerization reactions impedes the industrial use thereof in economic terms and in terms of short or even continuous production cycles.

Thus, the inventors did not pursue this avenue.

According to the invention, the problem is solved by using microcapsules prepared from oligomers of poly(beta-amino)ester (abbreviated here as PBAE) by radical polymerization. This reaction leads to microcapsules comprising a wall made of a crosslinked polymer of the PBAE type.

According to the invention, an O/W emulsion (Oil in Water) comprising at least one so-called active substance, a surfactant, at least one poly(beta-amino ester) prepolymer (functionalized at chain ends by acrylate functions) and optionally one or two vinyl monomers X1 and/or X2 are provided, the polymerization is initiated within said emulsion, and the polymerization reaction is allowed to continue. In general, the monomers X1 and/or X2, which are optional, are selected from (meth)acrylates. A polymerization initiator is present in the internal phase and/or in the aqueous phase.

Poly(beta-amino ester)s are known per se and have been used substantially in recent years (Lynn, D. M.; Langer, R. J. Am. Chem. Soc. 2000, 122 (44), 10761-10768; Liu, Y.; Li, Y.; Keskin, D.; Shi, L. Adv. Healthcare Mater. 2018, 2 (2), 1801359-24) thanks to the biocompatibility and biodegradability properties thereof, and they now represent a family of materials which have numerous applications as biomaterials (for example as anticancer drug vector, as antimicrobial material, and for tissue engineering).

It is also known that linear or crosslinked PBAEs are relatively stable in neutral medium but are degraded more rapidly by ester function hydrolysis at acid and/or basic pH. This hydrolysis phenomenon results in the release of small molecules such as bis((3-amino acid)s and diols when linear PBAEs are used; these molecules are known to be non-toxic with respect to mammalian cells, and to have a weak influence on the metabolism of healthy cells.

According to an essential feature of the present invention, the microcapsules having a PBAE wall are synthesized by radical polymerization. The inventors have found that this process, applicable to various active ingredients to be encapsulated, makes it possible to prepare stable microcapsules which can be isolated by drying and which have the property of being (bio)degradable.

According to another essential feature of the process according to the invention, the prepolymer is a beta-aminoester prepolymer (the latter being abbreviated here as BAE), and preferably a branched PBAE prepolymer.

The microencapsulation process according to the invention comprises the following steps:

(a) Preparation of an oily phase comprising:
  - a beta-aminoester prepolymer,
  - an active substance, possibly in organic solution, constituting the phase to be encapsulated,
  - optionally one or two monomers X1 and/or X2,
  - optionally an initiator of polymerization;

(b) Preparation of an aqueous phase comprising at least one surfactant; and optionally a polymerization initiator;

(c) Preparation of an emulsion of the O/W type (Oil in Water) by adding said oily phase to said aqueous phase;

(d) Initiation of radical polymerization within said emulsion;

(e) Continuation of the polymerization, preferably at a temperature between approximately 20° C. and 100° C., to form PBAE microcapsules containing the said phase to be encapsulated;

(f) Optionally, collection, washing and drying of the microcapsules.

The order of steps (a) and (b) can be reversed. The presence of a polymerization initiator is necessary, it can be present in the oily phase and/or in the aqueous phase. Said oily phase is advantageously a homogeneous phase.

Said prepolymer of a poly(beta-aminoester) can be prepared by solution polymerization of multi-acrylate and multi-amine compounds. It is soluble in an oily phase.

Thus, a first object of the invention is a process for manufacturing microcapsules comprising a wall containing a so-called active substance, process in which:

- a prepolymer of a poly(beta-aminoester), said active substance, optionally one or two monomers X1 and/or X2, a polymerization initiator and an aqueous solution of at least one surfactant are provided;
- an oily phase is prepared comprising said prepolymer, said active substance and the monomer(s) X1 and/or X2, if present;
- knowing that said polymerization initiator can be introduced into said oily phase and/or into said aqueous solution;
- an emulsion of O/W type is prepared by adding said oily phase to said aqueous solution of surfactant;
- the polymerization is initiated within said emulsion,
- the polymerization reaction is allowed to continue.

Said microcapsules have a biodegradable polymer wall. Said polymer is a crosslinked polymer of the poly(beta-amino ester) type.

The presence of X1 and/or X2 monomers is optional, the prepolymer of a poly(beta-aminoester) being capable of polymerizing on itself, especially if it has been prepared by a process which will be described below. It is preferred that the cumulative mass of monomers X1 and X2 does not exceed 40% of the total mass of monomers X1+X2 and of the PBAE prepolymer.

Said monomer X1 is selected from vinyl monomers. It can be selected so as to obtain a microcapsule wall having desired properties. For example, the use of a monomer X1 such as methyl methacrylate or isobornyl methacrylate increases the value of the glass transition temperature Tg of the polymer obtained, whereas the use of a monomer X1 such as butyl methacrylate or a linear alkyl acrylate decreases the value of Tg of the polymer obtained.

Said X2 monomer is also selected from vinyl monomers, but it is a monomer of polymerizable surfactant type (also called "surfmer") or reactive surfactant. These X2 monomers may or may not be charged: they may be neutral with PEG or alcohol functions, anionic with a carboxylic acid such as acrylic acid, methacrylic acid, or cationic, or even zwitterionic (for example molecules of the 3-[[2-(Acryloyloxy)ethyl]-dimethylammonio]propane-1-sulfonate type).

Said poly(beta-aminoester) prepolymer can be prepared by reaction between an amine and a multiacrylate. Said prepolymer must be a prepolymer soluble in the active phase. Said amine is selected from functional primary amines and/or functional secondary amines, and more particularly from the group formed by:

- primary amines R—$NH_2$;
- primary diamines of the $NH_2(CH_2)_nNH_2$ type where n is an integer which can typically be between 1 and 20, and which is preferably 2 or 6;
- primary diamines comprising an aromatic core such as meta-xylylene diamine;
- primary (multi)amines such as tris(2-aminoethyl)amine;
- secondary diamines such as piperazine;
- (multi)amines containing primary and secondary amine functions such as tetraethylene pentamine;
- polymers containing primary and/or secondary amine functions such as polyethylene imine.

By primary (multi)amine is meant any compound comprising at least two primary amine functions.

Said multiacrylate is advantageously a (multi)acrylate of formula X'—(—O(C═O)—CH═$CH_2$)$_n$ with n>2 and where X' represents a molecule on which n acrylate units are grafted. More specifically, it is advantageously selected from the group formed by:

- diacrylates, and preferably those described in the article by Nayak et al. (S. Dev Maurya, S. K. Kurmvanshi, S. Mohanty & S. K. Nayak (2018), "A Review on Acrylate-Terminated Urethane Oligomers and Polymers: Synthesis and Applications", Polymer-Plastics Technology and Engineering, 2018, 57, 7, 625-656, DOI: 10.1080/03602559.2017.1332764);
- triacrylates, in particular $C_{15}O_6H_2O$ (CAS No. 15625-89-5, i.e. trimethylolpropane triacrylate), tetraacrylates, pentaacrylates, hexaacrylates, mixtures between these different acrylates of the $O[CH_2C(CH_2OR)_3]_2$ type where R is H or COCH═$CH_2$;
- the (multi)acrylates described in the article by Nayak et al. (S. Dev Maurya, S. K. Kurmvanshi, S. Mohanty & S. K. Nayak (2018), "A Review on Acrylate-Terminated Urethane Oligomers and Polymers: Synthesis and Applications", Polymer-Plastics Technology and Engineering, 2018, 57, 7, 625-656, DOI: 10.1080/03602559.2017.1332764);
- polymers bearing pendant acrylate functions;
- the mixture of different compounds described above.

The wall of the microcapsules thus prepared can be modified by adding a polymer layer deposited on the surface of the microcapsules. This deposition can be performed by adding a polymer dispersed in an aqueous phase which will be deposited on the surface of the capsules. Among these polymers, mention can be made of polysaccharides (for example, cellulose, starch, alginates, chitosan) and derivatives thereof.

Another possibility for modifying the wall of the microcapsules is that of modifying it by adding a radical initiator either in the aqueous phase or in the oily phase. A final possibility is that of reacting the residual surface amine functions with water-soluble monofunctional acrylates to modify the surface condition of the microcapsules.

Another object of the invention are microcapsules capable of being obtained by the process according to the invention.

FIGURES

FIG. 1 shows the general diagram of the process according to the invention. The four-digit numerals designate steps in this process. The ingredient in parentheses is optional, the ingredient marked with an asterisk (*) can be present in either solution, but is necessary for the reaction to take place.

DETAILED DESCRIPTION

In the context of the present invention, the terms "oligomer" and "prepolymer" are used as defined in the Compendium of Chemical Terminology ("Gold Book") published by the International Union of Pure and Applied Chemistry (IUPAC), version 2.3.3 (2014 Feb. 24); the IUPAC terminology work is a reference for a person skilled in the field of chemistry.

In this respect, an "oligomer" is a substance composed of oligomeric molecules; an "oligomeric molecule" is a molecule of intermediate relative molecular mass, the structure of which consists essentially of a small plurality of units derived, actually or conceptually, from molecules of lower relative molecular mass. In this context, a molecule is considered to have an "intermediate" molecular mass if its properties change significantly when one or a few of these units are removed.

Also in this respect, a "pre-polymer" is a polymer or oligomer composed of pre-polymer molecules; a "pre-polymer molecule" is a macromolecule or an oligomeric molecule capable of entering, via reactive terminal groups, into subsequent polymerization, contributing more than one monomer unit to at least one chain of the final macromolecule.

In the detailed description which follows, embodiments of the present description and numerous specific details are set forth in order to provide a more thorough understanding of the present invention, and in order to enable a person skilled in the art to carry out the invention. However, it will be apparent to those skilled in the art that the present description can be implemented without these specific details. In other cases, well-known features have not been described in detail to avoid unnecessarily overloading the description.

FIG. 1 shows a general diagram of the process according to the invention. The aqueous solution of the surfactant (1000) is prepared. An organic solution (also called "oily phase") is also prepared, comprising the phase to be encapsulated (which comprises the so-called active substance), the monomers X1 and/or X2 (which are optional) and a prepolymer of PBAE (1002). The initiator, which is necessary for the reaction, is in the aqueous solution 1000 and/or in the oily phase 1002.

At step 1010, this oily phase 1002, which is an organic solution, is added to said aqueous solution 1000, and at step 1020 an emulsion 1022 of the O/W type ("Oil in Water", according to a designation known to those skilled in the art), is obtained. In this emulsion, said organic solution is the so-called oily phase (O phase). In step 1040, said emulsion is slowly heated with stirring to a temperature sufficient to initiate radical polymerization. The polymerization reaction leads to a reaction mixture 1042 from which gradually forms in step 1050 a heterogeneous mixture 1052 called slurry which comprises, in aqueous-based suspension, the microcapsules containing the phase to be encapsulated.

Step 1050 typically involves a temperature of reaction mixture 1042 above about 30° C., typically between 30° C. and 100° C. A temperature between about 30° C. and about 90° C. is preferred, and even more preferably between about 60° C. and about 80° C.

This process can be applied to different X1 and/or X2 monomers and to different PBAE prepolymers.

As indicated above, said poly(beta-aminoester) prepolymer can be prepared by reaction between an amine and a multiacrylate. We give here a non-exhaustive list of diacrylates which can be used: 1,6-hexanediol diacrylate (HDDA), Tripropylene glycol diacrylate (TPGDA), Tricyclodecan dimethanol diacrylate, bisphenol A-diethyl ether diacrylate (BHEDA).

We give here a non-exhaustive list of (multi)acrylates which can be used: Trimethylol propane triacrylate (TMPTA), dipentaerythritol penta/hexa acrylate (DPHPA), pentaerythritol tetraacrylate (PETEA), tris(2-hydroxyethyl) isocyanate triacrylate, trimethylpropane tetraacrylate.

The presence of an initiator is necessary. It can be introduced into the oily phase and/or into the aqueous phase.

An azo type initiator can be used.

Among the azo initiators which can be introduced into the aqueous phase, the following are mentioned here:

2,2'-Azobis[2-methyl-N-(2-hydroxyethyl)propionamide] (CAS no: 61551-69-7), 2,2'-Azobis(2-methylpropionamidine)dihydrochloride (CAS no: 2997-92-4), 2,2'-Azobis[2-(2-imidazolin-2-yl)propane]dihydrochloride (CAS no: 27776-21-2), 4,4'-Azobis(4-cyanovaleric acid) (CAS no: 2638-94-0), 2,2'-Azobis[2-(2-imidazolin-2-yl)propane] (CAS no: 20858-12-2), 2,2'-Azobis [N-(2-carboxyethyl)-2-methylpropionamidine] tetrahydrate (CAS no: 1400693-47-1).

Among the azo initiators which can be introduced into the oily phase, the following are mentioned here:

Dimethyl 2,2'-azobis(2-methylpropionate) (CAS no: 2589-57-3), 2,2'-Azobis(4-methoxy-2,4-dimethylvaleronitrile) (CAS no: 15545-97-8), 1,1'-Azobis(cyclohexane-1-carbonitrile (CAS no: 2094-98-6), 2,2'-Azobis(isobutyronitrile) (CAS no: 78-67-1), 2,2'-Azobis(2,4-dimethylvaleronitrile) (CAS no: 4419-11-8), 2,2'-Azobis(N-butyl-2-methylpropionamide (CAS no: 195520-32-2), 2,2'-Azobis(2-methylbutyronitrile) (CAS no: 13472-08-7).

All of these products are commercially available.

It is also possible to use an initiator of the peroxidic type, of which there are a very large number on the market. It is also possible to use red-ox systems comprising a compound of the potassium persulfate type (known by the acronym KPS) or ammonium persulfate type (known by the acronym APS) and an inorganic reductor (for example of the $FeSO_4$ type) or an organic reductor (for example of the metabisulphite type).

The organic core of the microcapsules can consist of an organic phase comprising an active substance. During the formation of the microcapsule, this organic (oily) phase will be enclosed by the polymeric wall of the microcapsule, which protects it from the environment. Said organic (oily) phase can consist of said active substance, or said active substance can be part of said organic (oily) phase, wherein it can be particularly dissolved. The expression "active substance" refers here to the specific purpose wherein the microcapsules are intended to be used; as a general rule, in view of the specificity of the microcapsule product, this purpose is always known during the manufacture thereof.

The active substance can be selected particularly from oils (pure or containing possibly other molecules in solution or in dispersion), such as essential oils, natural and edible oils, plant and edible oils, liquid alkanes, esters and fatty acids, or from dyes, inks, paints, thermochromic and/or photochromic substances, fragrances, products with biocidal effect, products with fungicidal effect, products with antiviral effect, products with phytosanitary effect, pharmaceutical active ingredients, products with cosmetic effect, adhesives; these active ingredients being optionally in the presence of an organic vector.

It is possible to use, non-restrictively, distillation extracts of natural products such as essential oils of eucalyptus, citronella, lavender, mint, cinnamon, camphor, aniseed, lemon, orange, which can be obtained by extraction from plant matter, or by synthesis.

It is also possible to use other substances such as long-chain alkanes (for example tetradecane), which can contain lipophilic solutions in solution.

As a general rule, and according to the function sought for the microcapsules, it is possible to use any hydrophobic compound, which will thus be naturally dispersed in the form of emulsion of hydrophobic droplets suspended in an aqueous phase.

Numerous additives enabling superior protection of the organic (oily) phase to be encapsulated, against infrared radiation, ultraviolet radiation, unintentional entry of specific gas or oxidation, can be incorporated in the microcapsule.

The wall of the microcapsules can be modified by adding a coating on the surface thereof. This deposition can be performed by adding a polymer dispersed in an aqueous phase which will be deposited on the surface of the capsules. Of these polymers, mention can be made of polysaccharides (cellulose, starch, alginates, chitosan, etc.) and derivatives thereof. This addition can be performed either hot or at ambient temperature at the end of the interfacial polymerization step.

The wall of the microcapsules can also be modified by adding a radical initiator either in the aqueous phase or in the organic (oily) phase. The addition in the organic phase can be performed before and/or after preparing the PBAE wall. If the addition is performed afterwards, the radical initiator can be diluted in acetone to promote transport in the microcapsules. These initiators can be azo compounds (such as azobis-isobutyronitrile and derivatives thereof) or peroxide compounds (lauroyl peroxide, etc.). In the case of initiators added in the aqueous phase, they can consist particularly of water-soluble azo compounds (such as 2,2'-Azobis(2-methylpropionamidine)dihydrochloride) red-ox systems (ammonium or potassium persulfate in combination with potassium metabisulfate for example). In an inert atmosphere, the radicals from the decomposition of the radical initiators can be added to the residual acrylate functions of the PBAE wall and reinforce it mechanically and/or modify the polarity thereof.

Another way to modify the wall of the microcapsules is to react the residual surface amine functions with water-soluble monofunctional acrylates. Without wishing to be bound to this hypothesis, the inventors believe that via Michael addition, an amino-ester bond would be formed and would anchor a functional group on the surface. Of the water-soluble acrylates suitable for use, mention can be made of acrylic acid, 2-carboxyethyl acrylate, 2-(dimethylamino) ethyl acrylate, 2-hydroxyethyl acrylate, poly(ethylene glycol) acrylates, 3-sulfopropyl acrylate potassium salt.

As surfactant, it is possible in particular to use nonionic surfactants, such as polyvinyl pyrrolidone (PVP), polyethylene glycol sorbitan monopalmitate (known under the trade mark Tween 20™), polyethylene glycol sorbitan monolaurate (known under the trade mark Tween 40™) polyethylene glycol sorbitan monooleate (known under the trademark Tween 80™), or ionic surfactants, such as partially neutralized salts of polyacrylic acids such as sodium or potassium polyacrylate or polymethacrylate, or sodium lignosulfate. It is possible to use copolymers of acrylic acid-alkyl acrylate, polyacrylic acid, polyoxyalkylene fatty esters. It is possible to use those surfactants which are cited in Encyclopedia of Chemical Technology, volume 8, pages 912 to 915, and which have a hydrophilic-lipophilic balance (according to the HLB system) equal to or greater than 10.

Other macromolecular surfactants can also be used. Mention can be made for example of polyacrylates, methylcelluloses, carboxymethylcelluloses, polyvinyl alcohol (PVA) optionally partially esterified or etherified, polyacrylamide or synthetic polymers having anhydride or carboxylic acid functions such as ethylene/maleic anhydride copolymers. Preferably, polyvinyl alcohol can be used as a surfactant.

It may be necessary, for example in the case of aqueous solutions of a cellulose compound, to add a little alkaline hydroxide such as sodium hydroxide, in order to facilitate the dissolution thereof; such cellulose products can also be used directly in the form of the sodium salts thereof for example. Pluronics type amphiphilic copolymers can also be used. Generally, aqueous solutions containing from 0.1 to 5 wt. % of surfactant are used.

The size of the droplets is dependent on the nature and the concentration of the surfactant and the stirring speed, the latter being chosen particularly high in that smaller mean droplet diameters are sought.

In general, the stirring speed during the preparation of the emulsion is from 5000 to 10,000 rpm. The emulsion is usually prepared at a temperature between 15° C. and 95° C.

Generally, when the emulsion has been obtained, impeller stirring is stopped and the emulsion is stirred using a common type of slower stirrer, for example of the frame stirrer type, typically at a speed of the order of 150 to 1500 rpm.

The method according to the invention thus results in homogeneous and fluid suspensions containing, according to the fillers introduced, generally from 20 wt. % to 80 wt. % of microcapsules having a mean diameter of 100 nm to 100 μm. The diameter of the microcapsules can be preferably between 1 μm and 50 μm, and more preferably between 10 μm and 40 μm.

The microcapsules, and in particular the wall thereof, according to the invention are (bio)degradable. The biodegradation can be determined for example by one of the methods described in the document "OECD Guidelines for Testing of Chemicals: Ready Biodegradability" (adopted by the OECD Council on Jul. 17, 1992). In particular, the manometric respirometry test (method 301 F) can be used. Preferably, this test is used on emptied and washed microcapsules, so that the biodegradation of the content of the microcapsules does not interfere with the test which is aimed at characterizing the biodegradation of the material forming the wall of the microcapsules. Preferably, the microcapsule according to the invention, and/or the wall thereof, shows a biodegradation of at least 60%, preferably at least 70%, more preferably at least 80%, measured after 10 days of incubation using said method 301 F. With the same method, after 28 days of incubation, the microcapsules according to the invention preferably show a biodegradation of at least 70%, preferably at least 80%, more preferably at least 90%, and more preferably at least 95%.

EXAMPLES

To allow a person skilled in the art to reproduce the invention, examples of implementation are given here; they do not restrict the scope of the invention.

Example 1

(i) Preparation of the Branched Poly(PAE) Prepolymer

In a flask with a closed cap, 1,6-hexanediol diacrylate monomer (80% Aldrich, 3.0 g) and tetraethylene pentamine (Technical Aldrich grade, 0.4 g) were stirred at room temperature until a homogeneous solution was obtained. Then, the reaction mixture was heated and stirred at 40° C. for 1 h, then for 30 min at room temperature, to obtain a mixture comprising the viscous branched poly(beta-aminoester) prepolymer and the excess of 1,6-hexanediol diacrylate.

This reaction is illustrated in the reaction scheme below.

[Chem 1]

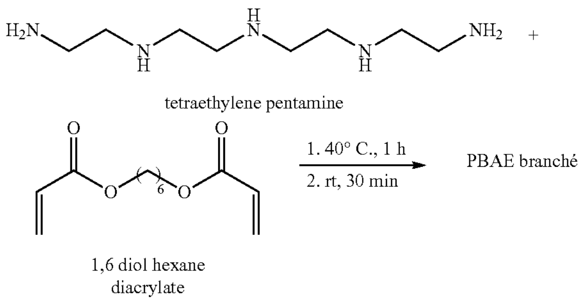

tetraethylene pentamine 1,6 diol hexane diacrylate (ii) Microencapsulation

A perfume, methylacrylic acid, methyl methacrylate and lauryl peroxide were placed in the flask containing the branched PBAE and the excess 1,6-hexandiol diacrylate, as obtained in step (i) above. This mixture was stirred at 30° C. until a homogeneous solution was obtained. It was then gradually added to a PVA solution (2%) prepared beforehand, preheated to 30° C. The resulting mixture was homogenized using an Ultraturrax™ at about 700 rpm to 800 rpm for 4 min to 10 mm at 30° C. to form an emulsion.

This emulsion was added to a single neck flask (100 mL) and stirred at 30° C. The emulsion was then degassed by bubbling argon with stirring at 30° C. for 60 min. Then, the emulsion was slowly heated (1° C./min) to 70° C. and stirred under an argon atmosphere for 18 h. Microcapsules were thus obtained with a wall of the PBAE type containing a perfume.

Example 2: Biodegradation Test

A batch of microcapsules prepared according to Example 1 was supplied. The dry microcapsules containing essential oil (Eucalyptus) were subjected to the biodegradability test described in document OECD 301 ("OECD Guideline for the Testing of Chemicals: Easy Biodegradability") using the method 301 F (Manometric respirometry test). After an incubation period of nineteen days the percentage of biodegradation was 70%.

Example 3: Biodegradation Test

A batch of microcapsules prepared according to Example 1 was supplied. The microcapsules were opened, emptied and washed. They were then subjected to the biodegradability test described in document OECD 301 ("OECD Guideline for the Testing of Chemicals: Easy Biodegradability") using method 301 F (Manometric respirometry test). After an incubation period of twenty-eight days the percentage of biodegradation was 85%.

The invention claimed is:

1. A process for manufacturing microcapsules comprising a wall made of a polymer material and containing an active substance, comprising:

(a) preparing an oily phase comprising
a poly (beta-aminoester) prepolymer
and the active substance, (b) preparing an aqueous phase comprising a surfactant;

(c) preparing an oil-in-water emulsion by adding said oily phase to said aqueous phase;

(d) initiating a radical polymerization within said emulsion; and (e) recovering the microcapsules after the radical polymerization wherein an order of steps (a) and (b) can be reversed.

2. The process according to claim 1, wherein the polymeric material of the wall is a crosslinked poly (beta-aminoester) polymer.

3. The process according to claim 1, wherein the oily phase further comprises at least one of a first monomer and a second monomer, wherein the first monomer is selected from the group consisting of methyl methacrylate, isobornyl methacrylate, butyl methacrylate, and linear alkyl acrylates; and wherein the second monomer is a polymerizable surfactant or a reactive surfactant monomer; and wherein at least one of the oily phase and the aqueous phase comprises a polymerization initiator.

4. The process according to claim 1, wherein the prepolymer of a poly (beta-aminoester) is obtained by the reaction between an amine and a multiacrylate.

5. Process according to claim 4, wherein the multiacrylate is selected from the group formed by diacrylates, triacrylates, trimethylolpropane triacrylate, tetraacrylates, pentaacrylates, hexaacrylates, and mixtures between these various acrylates of the $O[CH_2C(CH_2OR)_3]_2$ –type where R is H or $COCH{=}CH_2$.

6. The process according to claim 4, wherein the amine is selected from the group consisting of functional primary amines and/or functional secondary amines, primary amines of the $R{-}NH_2$ type; primary diamines of the $NH_2(CH_2)_nNH_2$ type, where n is an integer between 1 and 20; primary diamines of the $NH_2(CH_2)_nNH_2$ type, where n is 2 or 6; primary diamines having an aromatic core; meta-xylylene diamine; primary (multi)amines; tris(2-aminoethyl)amine; (multi)amines containing primary and secondary amine functions; tetraethylene pentamine; secondary diamines; piperazine; polymers containing primary and or secondary amine functions; and polyethylene imine.

7. The process according to claim 1, wherein the surfactant is a macromolecular surfactants.

8. The process according to claim 1, wherein the active substance is selected from the group consisting of:

essential oils and fragrances, inks, paints, thermochromic and/or photochromic substances, dyes, glues, products with a biocidal effect, products with a fungicidal effect, products with an antiviral effect, products with a phytosanitary effect, products with a cosmetic effect, active pharmaceutical ingredients, and natural and edible oils, vegetable and edible oils, liquid alkanes, esters and fatty acids.

9. The process according to claim 1, wherein the wall of the microcapsules is modified either by a layer of polymer deposited on the surface of the microcapsules, or by the addition of a radical initiator in the aqueous phase and/or the oily phase, or by adding to the aqueous phase a water-soluble acrylate capable of modifying the surface state of the microcapsules.

10. A microcapsule obtained by the process according to claim 1.

11. The microcapsule according to claim 10, wherein at least one of the microcapsule and the wall of the microcapsule shows a biodegradation of at least 60%, measured by a manometric respirometry test according to method 301 F of the "OECD Guidelines for the Testing of Chemical Products: Ready Biodegradability" after a ten-day incubation.

12. The microcapsule according to claim 10, wherein at least one of the microcapsule and the wall of the microcapsule shows a biodegradation of at least 85%, measured by a manometric respirometry test according to method 301 F of the "OECD Guidelines for the Testing of Chemicals: Ready Biodegradability" after incubation for 28 days.

13. The microcapsule according to claim 10, wherein the wall of the microcapsule is modified either by a layer of polymer deposited on a surface of the microcapsule, either by adding a radical initiator to the aqueous phase and/or the oily phase, or by adding a water-soluble acrylate capable of modifying a surface state of the microcapsules to the aqueous phase.

14. The process according to claim 7, wherein the macromolecular surfactant is selected from the group consisting of polyacrylates, methylcelluloses, carboxymethylcelluloses, polyvinyl alcohol, partially esterified polyvinyl alcohol, partially etherified polyvinyl alcohol, polyacrylamide, synthetic polymers having anhydride or carboxylic acid functions, ethylene/maleic anhydride copolymers, and polyvinyl alcohol.

* * * * *